United States Patent

Nedelec et al.

[11] Patent Number: 4,565,656
[45] Date of Patent: * Jan. 21, 1986

[54] PREPARATION OF 17β-HYDROXYACETYL-17α-OL-STEROIDS

[75] Inventors: Lucien Nedelec, Le Raincy; Vesperto Torelli; Michel Hardy, both of Maisons-Alfort, all of France

[73] Assignee: Roussel Uclaf, Paris, France

[ * ] Notice: The portion of the term of this patent subsequent to Aug. 7, 2001 has been disclaimed.

[21] Appl. No.: 343,357

[22] Filed: Jan. 27, 1982

[30] Foreign Application Priority Data

Jan. 29, 1981 [FR] France .................. 81 01688

[51] Int. Cl.$^4$ .................................. C07J 3/00
[52] U.S. Cl. .................... 260/397.47; 260/397.1; 260/239.55 C; 260/397.4; 260/397.5
[58] Field of Search .................. 260/397.47

[56] References Cited

U.S. PATENT DOCUMENTS

| | | | |
|---|---|---|---|
| 3,793,350 | 2/1974 | Crabbe et al. | 260/397.47 |
| 4,150,044 | 4/1979 | Heineman et al. | 260/397.47 |
| 4,155,923 | 5/1979 | Neef et al. | 260/397.47 |

OTHER PUBLICATIONS

Boar et al., "Journal of the Chemical Soc., Perkin, Transactions I 1975, pp. 1242–1244.

*Primary Examiner*—Elbert L. Roberts
*Attorney, Agent, or Firm*—Bierman, Peroff & Muserlian

[57] ABSTRACT

A novel process for the preparation of 17β-hydroxyacetyl-17α-ol-steroids of the formula

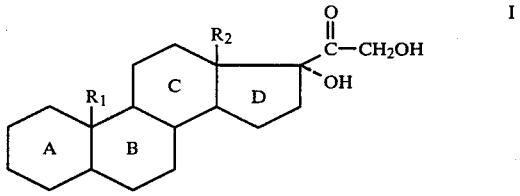

wherein $R_1$ is selected from the group consisting of hydrogen, alkyl of 1 to 4 carbon atoms optionally substituted with halogen or an oxygen or nitrogen function and alkenyl and alkynyl of 2 to 4 carbon atoms, $R_2$ is alkyl of 1 to 4 carbon atoms and the A,B,C and D rings may contain one or more double bonds and are optionally substituted with at least one member of the group consisting of hydroxy, keto, halogen, alkyl and alkoxy of 1 to 4 carbon atoms and alkenyl and alkynyl of 2 to 4 carbon atoms which compounds are generally known of the cortisonic type with known properties.

9 Claims, No Drawings

PREPARATION OF 17β-HYDROXYACETYL-17α-OL-STEROIDS

STATE OF THE ART

Boar et al [Journal of the Chemical Society, Perkin, Transactions I (1975), p. 1242–1244] describes the reaction of lead tetraacetate with a steroid containing in the 17-position the group

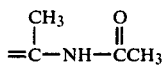

as well as the reaction of lead tetraacetate with a steroid having in the 17-position the

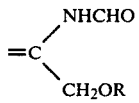

wherein R is hydrogen or a protecting group.

Copending, commonly assigned U.S. patent application Ser. No. 173,172 filed July 28, 1980 describes compounds having in the 17-position the group

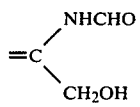

which are used as intermediates to form desoxycortisone type compounds.

OBJECTS OF THE INVENTION

It is an object of the invention to provide a novel process for the preparation of the compounds of formula I.

It is another object of the invention to provide novel intermediates prepared in the novel process for the preparation of compounds of formula I.

These and other objects and advantages of the invention will become obvious from the following detailed description.

THE INVENTION

The novel process of the invention for the preparation of 17β-hydroxyacetyl-17α-ol-steroids of the formula

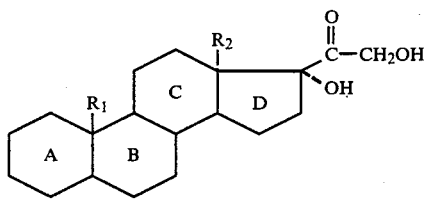

wherein $R_1$ is selected from the group consisting of hydrogen, alkyl of 1 to 4 carbon atoms optionally substituted with halogen or an oxygen or nitrogen function and alkenyl and alkynyl of 2 to 4 carbon atoms, $R_2$ is alkyl of 1 to 4 carbon atoms and the A,B,C and D rings may contain one or more double bonds and are optionally substituted with at least one member of the group consisting of hydroxy, keto, halogen, alkyl and alkoxy of 1 to 4 carbon atoms and alkenyl and alkynyl of 2 to 4 carbon atoms comprises reacting a compound of the formula

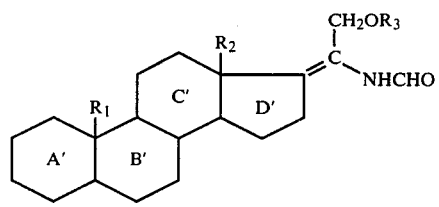

wherein $R_1$ and $R_2$ have the above definition, $R_3$ is selected from the group consisting of hydrogen and $R_3'$, $R_3'$ is a group protecting the hydroxyl and A',B',C' and D' have the same definition as A,B,C and D with the supplemental possibility of being substituted with a protected hydroxyl or protected ketone with a reactant capable of introducing an acetoxyl group to obtain a compound of the formula

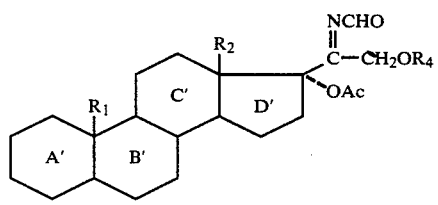

wherein $R_4$ is selected from the group consisting of $R_3'$ and acetyl and Ac is acetyl, reacting the latter with a hydrolysis agent to obtain a compound of the formula

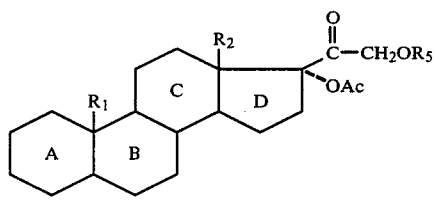

wherein $R_1$, $R_2$, A,B,C and D have the above definitions and $R_5$ is selected from the group consisting of hydrogen, a non-easily hydrolyzable hydroxy protective group and an acetyl group and reacting the latter to eliminate the acetyl group in the 17α-position and the $R_5$ group where it is other than hydrogen to obtain the corresponding compound of formula I.

The starting compounds of formula II may be in the form of its 20(E) isomer or 20(Z) isomer or mixtures of the 20(E) and 20(Z) isomers.

Examples of $R_1$ are alkyl such as methyl, ethyl, propyl, isopropyl, n-butyl, sec.-butyl and tert.-butyl; alkyl substituted with oxygen and nitrogen functions such as hydroxymethyl, hydroxyethyl, formyl, acetyl, cyano, aminomethyl and aminoethyl; haloalkyl such as halomethyl wherein the halogen is chlorine, bromine or fluorine; alkenyl such as vinyl and allyl; and alkynyl such as ethynyl. Examples of $R_2$ are methyl, ethyl, propyl and butyl, preferably methyl or ethyl.

When the A,B,C and D rings contain one or more double bonds, the double bonds are preferably in 1(2), 4(5), 5(6) or 9(11) positions or a conjugated double bond system such as 3(4) and 5(6) or 4(5) and 6(7) or an aromatic system such as 1,3,5 positions or a triple bond system such as 1(2), 4(5), 6(7).

When the A,B,C and D rings are substituted with at least one hydroxy group, they are preferably in the 3- and/or 11-positions. When the A,B,C and D rings are substituted with at least one keto group, they are preferably in the 3- and/or 11-position. When the A,B,C and D rings contain at least one halogen, they are preferably fluorine, chlorine or bromine in the 6- and/or 9-positions.

When the A,B,C and D rings are substituted with at least one alkyl, they are preferably methyl or ethyl in the 2,6,7,16α and/or 16β-positions. When the A,B,C and D rings are substituted with at least one alkoxy, they are preferably methoxy or ethoxy in the 3- and/or 11β-positions. When the A,B,C and D rings are substituted with at least one alkenyl, they are preferably vinyl or allyl in the 11β-position. When the A,B,C and D rings are substituted with at least one alkynyl, they are preferably ethynyl in the 11β-position.

When the A',B',C' and D' rings contain protected hydroxyl or ketone groups, they are preferably in the 3- and/or 11-positions. The hydroxyl groups may be protected in a known manner such as acetonide groups, cyclic carbonates, orthoesters, cyclic sulfites, ether with tetrahydropyranyl, trityl and benzyl. The ketone groups may also be protected in a classical manner such as ketals, especially ethylene ketal, thioketals, hemithioketals, ethers of enols, acetates of enols, enamines or oximes. The preferred ketone protective groups are ketals, especially ethylene ketal. The preferred products are 3,3-ethylenedioxy-Δ$^5$ products or 3,3-ethylenedioxy-5α-ol products.

Among the compounds of formula II, the preferred products are those wherein R$_3$ is R$_3$' which is a group protecting the hydroxyl which protective groups are known in the literature. The preferred protective groups are acyl groups, especially acetyl. When the starting compound of formula II has R$_3$ as hydrogen, the 20-ol of group is changed to acetyl by reaction with a compound to introduce an acetoxy group. It is understood that the principal action of such a reactant is to introduce an acetoxy in the 17α-position and the preferred reactant is lead tetraacetate or iodosobenzene diacetate.

The acid hydrolysis agent used to react with the compound of formula III is preferably an acid hydrolysis agent such as hydrochloric acid, sulfuric acid, acetic acid or trifluoroacetic acid which converts the formylimino group into the ketone. The said treatment generally at the same time also removes the protective hydroxyl or ketone groups as the ketal group in free hydroxyl or ketone groups. At the same time, when R$_4$ is a protective group easily removable by acid hydrolysis, the group is also removed, especially when R$_4$ is tetrahydropyranyl.

When R$_4$ is a protective group not easily removable by acid hydrolysis such as an acyl group like acetyl, the group remains during the acid hydrolysis. The treatment of the compound of formula IV to remove the 17α-acetyl group and to remove the radical not easily removable by hydrolysis when R$_5$ is other than hydrogen such as acyl is preferably saponification under the usual conditions using a base such as sodium hydroxide, potassium hydroxide, baryta or a salt such as an alkali metal carbonate. To recover the resulting product in an easy manner, the reaction mixture is acidified with an acid such as hydrochloric acid, sulfuric acid or acetic acid.

Depending on the value of R$_5$, the preceding reaction may be followed by another reaction to remove the R$_5$ group such as hydrogenolysis under the usual conditions.

It is understood that the steps of the process which are especially important are the steps of introducing the acetoxyl and hydrolysis of the formylimino group. More particularly, the step of introducing the acetoxyl group is an essential step of the process of the invention. A preferred mode of the process uses the compounds of formula II wherein R$_2$ is methyl and R$_1$ is hydrogen, methyl or ethynyl.

A preferred mode of the process of the invention for the preparation of compounds of the formula

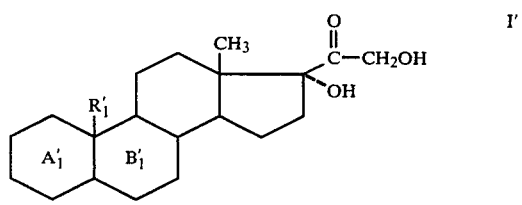

wherein R$_1$', A$_1$' and B$_1$' form a ring system selected from the group consisting of

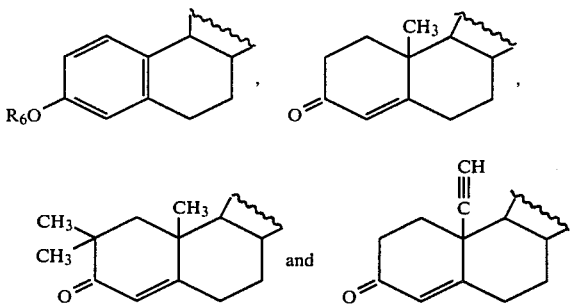

and R$_6$ is selected from the group consisting of alkyl of 1 to 8 carbon atoms and aralkyl of 7 to 12 carbon atoms comprises reacting a compound of the formula

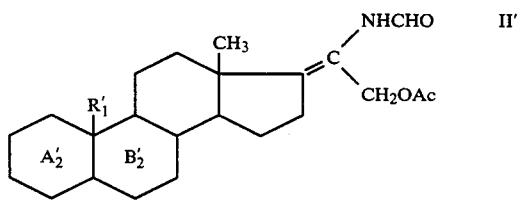

wherein the R$_1$', A$_2$' and B$_2$' form a group selected from the group consisting of

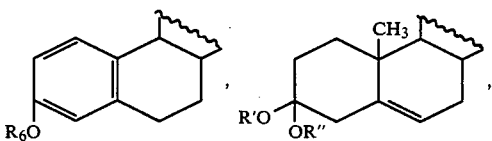

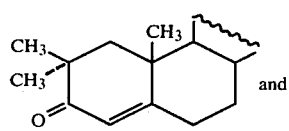
and

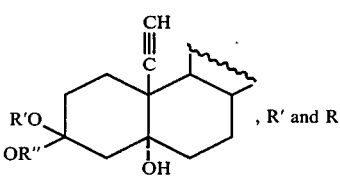
, R' and R"

are individually selected from the group consisting of methyl and ethyl or taken together are ethylene or trimethylene and Ac is acetyl with a reactant capable of introducing an acetoxy group to obtain a compound of the formula

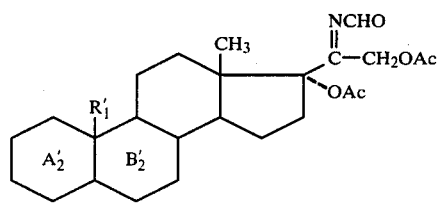   III' wherein R', Ac, $A_2'$ and $B_2'$ have the above definition and reacting the latter with a hydrolysis agent to obtain a compound of the formula

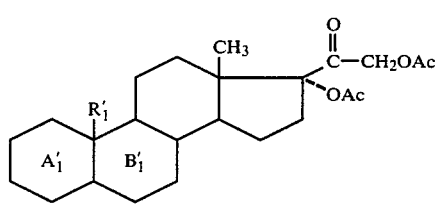   IV' and saponifying the latter to obtain the corresponding compound of formula I'.

As indicated above for the compounds of formula II, the compounds of formula II' may exist as 20(E) or 20(Z) isomers or mixtures thereof.

Among the preferred values of $R_6$ are methyl, ethyl or benzyl, especially methyl. R' and R" preferably together form ethylene.

The preferred reactant to introduce the acetoxy group is lead tetraacetate or iodosobenzene diacetate. The hydrolysis step is preferably effected with hydrochloric acid or acetic acid and the saponification of the compounds of formula IV' is effected preferably with potassium hydroxide followed by treatment with acetic acid.

A particularly preferred embodiment of the process of the invention for the preparation of compounds of the formula

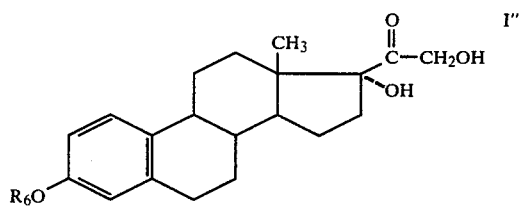   I"

wherein $R_6$ has the above definition comprises reacting a compound of formula II' wherein $R_1'$, $A_2'$ and $B_2'$ form the group

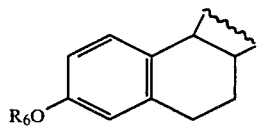

and it is preferred to introduce the acetoxy with lead tetraacetate.

It is clear that the process of the invention is at the same time a very general reaction for modifying the 17-position of the steroid molecule without in principle affecting the other positions of the molecule and has a great commercial interest as it permits the preparation of a series of cortisonic type compounds having the 17β-hydroxyacetyl-17α-ol group. Moreover, the starting materials of formula II are prepared by a novel process from the 17-one compounds and the process is very simple.

Another object of the invention are the novel intermediate compounds of the formulae

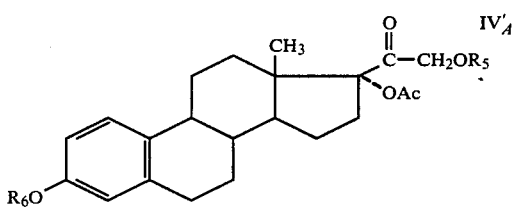   IV'$_A$

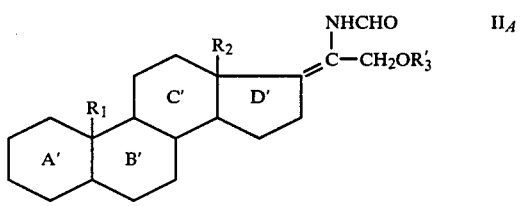   II$_A$ and

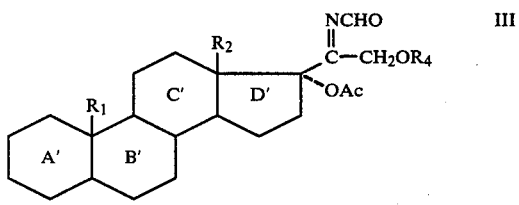   III wherein $R_1$, $R_2$, $A_1'$, $B_1'$, $C_1'$, $D_1'$, $R_3'$, $R_4$, $R_5$ and $R_6$ have the above definitions and more precisely the compounds of formulae II and III wherein $R_3$ and $R_4$ are both acetyl and the C' and D' rings are not substituted.

As indicated above, the compounds of formula I are for the most part known compounds of the cortisonic type with their known properties making them useful in the pharmaceutical industry such as Δ⁴-pregnene-17α,21-diol-3,20-dione.

However, the compounds of the formula

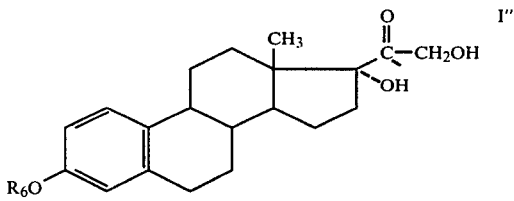

wherein R₆ is alkyl of 1 to 8 carbon atoms or aralkyl of 7 to 12 carbon atoms, such as 3-methoxy-19-nor-$^{1,3,5(10)}$-pregnatriene-17α,21-diol-20-one are new and are useful as medicaments or as intermediates to prepare pharmacologically active compounds.

The starting compounds of formula II may be prepared by reacting a compound of the formula

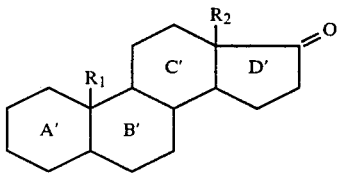

with a compound of the formula

wherein M is an alkali metal and R is alkyl of 1 to 18 carbon atoms to obtain a compound of the formula

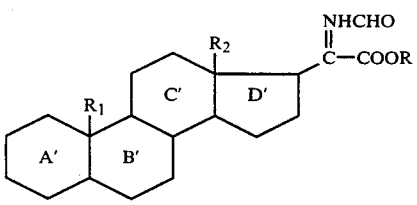

and reacting the latter with a reducing agent to obtain a compound of formula II wherein R₃ is hydrogen which may optionally be reacted with a reactive derivative to protect the hydroxyl group. The reducing agent is preferably of the formula

wherein M₁ is an alkali metal and AlK₁ and AlK₂ are individually alkyl of 1 to 8 carbon atoms. The preferred reactive derivatives of the protective group are acetyl chloride or acetic anhydride.

In the following examples there are described several preferred embodiments to illustrate the invention. However, it should be understood that the invention is not intended to be limited to the specific embodiments.

EXAMPLE 1

Δ⁴-pregnene-17α,21-diol-3,20-dione

Step A:

Ethyl (20Z) 3,3-ethylenedioxy-20-formamido-Δ$^{5,17(20)}$-pregnadiene-21-oate 8.6 ml of a solution of 2.6M potassium tert.-butylate in tetrahydrofuran were added dropwise with stirring under an inert atmosphere at 10° C. to a mixture of 2.5 ml of ethyl isocyanate and 40 ml of tetrahydrofuran in an ice bath and the mixture was rinsed with 5 ml of anhydrous tetrahydrofuran. The suspension was stirred at 15° C. for 10 minutes and 5.8 g of 3,3-ethylenedioxy-Δ⁵-androstene-17-one were added thereto all at once. The mixture was stirred at room temperature and then allowed to stand for one hour and was poured into aqueous saturated ammonium chloride solution. The mixture was extracted with dichloromethane and the organic phase was washed with water, dried and evaporated to dryness under reduced pressure. The 8.6 g of residue were empasted at reflux with 50 ml of ethyl acetate for 10 minutes and was iced and vacuum filtered. The product was rinsed with ethyl acetate to obtain 4.55 g of ethyl (20Z) 3,3-ethylenedioxy-20-formamido-Δ$^{5,17(20)}$-pregnadiene-21-oate which was crystallized from a dichloromethaneethyl acetate mixture to obtain 4.05 g of the said product melting at 214° C.

The combined mother liquors of crystallization were evaporated to dryness and the residue was chromatographed over silica gel. Elution with a 7-3 benzene-ethyl acetate mixture yielded 3.3 g of product which were empasted with ethyl acetate to obtain 2.62 g of pure product. Another 0.15 g of product was obtained from the mother liquors for a total of 6.82 g of product.

Step B:

(20Z) 3,3-ethylenedioxy-20-formamido-Δ$^{5,17(20)}$-pregnadiene-21-ol 3.5 ml of a solution of 3.5M of sodium dihydro bis(2-methoxyethoxy)-aluminate in toluene were added dropwise over 20 minutes at 3° C. with stirring under a nitrogen atmosphere to a solution of 2.26 g of the product of Step A in 33 ml of anhydrous tetrahydrofuran and the mixture was stirred under nitrogen at 3° C. for 2 hours. Then, 22 ml of ethanol and 1 g of sodium borohydride were slowly added to the mixture which was then stirred for 45 minutes at room temperature. A solution of Seignette salt (potassium and sodium double tartrate) was added to the mixture which was extracted with dichloromethane. The organic phase was washed with water, dried and evaporated to dryness to obtain 2.08 g of residue which was crystallized from a mixture of dichloromethane and isopropyl ether to obtain 1.78 g of product which was crystallized from ethanol to obtain (20Z) 3,3-ethylenedioxy-20-formamido-Δ$^{5,17(20)}$-pregnadiene-21-ol melting at 260° C.

Step C.

(20Z) 3,3-ethylenedioxy-20-formamido-21-acetoxy-Δ$^{5,17(20)}$-pregnadiene

A suspension of 3.54 g of the product of Step B, 35 ml of pyridine and 17 ml of acetic anhydride was stirred at room temperature for 90 minutes and excess acetic anhydride was destroyed by addition of a few ml of water. The mixture was diluted with water to a volume of 250 ml and was vacuum filtered. The crystals were washed with water and dried to obtain 3.8 g of (20Z) 3,3-ethylenedioxy-20-formamido-21-acetoxy-$\Delta^{5,17(20)}$-pregnadiene in the form of crystals melting at 216° C. After crystallization from a mixture of ethanolmethylene chloride, the product melted at 220° C.

Analysis: $C_{26}H_{39}O_7N$. Calculated: %C 70.40; %H 8.40; %N 3.15. Found: %C 70.2; %H 8.4; %N 3.2.

Step D:

3,3-ethylenedioxy-17α,21-diacetoxy-20-formylimino-$\Delta^5$-pregnene 4 g of dry lead tetraacetate were added all at once to a suspension of 3.57 g of the product of Step C in 200 ml of anhydrous benzene and the mixture was stirred for 50 minutes and was then poured into aqueous sodium bicarbonate solution. The two phases were emulsified and the mixture was vacuum filtered. The decanted aqueous phase was extracted with ethyl acetate and the combined organic phases were washed with water, dried and evaporated to dryness. The 4 g of residue was dissolved in dichloromethane containing 1% of triethylamine and the solution was diluted with isopropyl ether and concentrated by distillation of dichloromethane. The resulting suspension was iced and vacuum filtered to obtain 3.24 g of 3,3-ethylenedioxy-17α,21-diacetoxy-20-formylimino-$\Delta^5$-pregnene melting at 192° C.

Analysis: $C_{28}H_{39}O_7N$. Calculated: %C 67.04; %H 7.83; %N 2.79. Found: %C 67.1; %H 7.8; %N 2.7.

Step E: $\Delta^4$-pregnene-17α,21-diol-3,20-dione

A suspension of 250 mg of the product of Step D in 2.5 ml of acetic acid and 1 ml of water was stirred at room temperature for 45 minutes and was then diluted with water and poured into aqueous sodium bicarbonate solution. The mixture was extracted with dichloromethane and the organic phase was dried and evaporated to dryness. The 250 mg of residue were taken up in 5 ml of tetrahydrofuran and 1 ml of 2N hydrochloric acid was added to the mixture. The mixture was heated at 70° C. for 20 minutes and then was iced and diluted with water. The mixture was extracted with dichloromethane and the organic phase was washed with water, dried and evaporated to dryness to obtain 220 mg of 17α,21-diacetoxy-$\Delta^4$-pregnene-3,20-dione.

The latter product was taken up in 6 ml of methanol and the mixture was cooled in an ice bath while adding thereto 0.2 ml of potassium methanolate (15 g in 100 ml). The mixture was stirred for 90 minutes and then 0.2 ml of acetic acid were added. The mixture was diluted with water and extracted with dichloromethane. The organic phase was washed with water, dried and evaporated to dryness. The 180 mg of residue were chromatographed over silica gel and eluted with a 6-4 benzene-ethyl acetate mixture to obtain 130 mg of $\Delta^4$-pregnene-17α,21-diol-3,20-dione melting at 218° C.

EXAMPLE 2

3-methoxy-19-nor-$\Delta^{1,3,5(10)}$-pregnatriene-17α,21-diol-20-one

Step A:

(20Z) 3-methoxy-20-formamido-19-nor-$\Delta^{1,3,5(10),17(20)}$-pregnatetraene-21-ol A solution of 1.6 g of ethyl (20Z) 3-methoxy-20-formamido-19-nor-$\Delta^{1,3,5(10),17(20)}$-pregnatetraene-21-oate [prepared by process of Schollkopf et al., Chem. Ber., Vol. 109 (1976) p, 3964] in 32 ml of anhydrous tetrahydrofuran was stirred at 0° C. for 2 hours with 200 mg of potassium borohydride and 200 mg of double lithium aluminum hydride. Ethanol was added thereto dropwise to destroy excess double lithium aluminum hydride and the mixture was stirred at room temperature for one hour. The mixture was diluted with a solution of Seignette salt and was extracted with ethyl acetate. The organic phase was filtered, washed with water, dried and evaporated to dryness. The residue was triturated with isopropyl ether and the suspension was iced and vacuum filtered. The product was washed with isopropyl ether and dried to obtain 1.28 g of (20Z) 3-methoxy-20-formamido-19-nor$\Delta^{1,3,5(10),17(20)}$-pregnatetraene 21-ol which after crystallization from methanol melted at 191° C.

Step B:

(20Z) 3-methoxy-20-formamido-21-acetoxy-19-nor-$\Delta^{1,3,5(10),17(20)}$-pregnatetraene A suspension of 5.8 g of the product of Step A, 12 ml of pyridine and 12 ml of acetic anhydride was stirred at room temperature for 4 hours and the resulting solution was progressively diluted with water until crystallization started. The mixture was vacuum filtered and the filtrate was washed with water and evaporated to dryness under reduced pressure to obtain 6.65 g of crystals which were crystallized from ethanol and then ethyl acetate to obtain (20Z) 3-methoxy-20-formamido-21-acetoxy-19-nor-$\Delta^{1,3,5(10),17(20)}$-pregnatetraene melting at 125° C.

Analysis: $C_{24}H_{31}NO_4$. Calculated: %C 72.52; %H 7.86; %N 3.52. Found: %C 72.6; %H 7.9; %N 3.5.

Step C:

3-methoxy-20-formylimino-17α,21-diacetoxy-19-nor-$\Delta^{1,3,5(10)}$-pregnatriene A solution of 400 mg of the product of Step B in 50 ml of anhydrous benzene was admixed with stirring with 665 mg of dry lead tetracetate and the mixture was stirred at room temperature for 30 minutes. Water was added to the mixture which was then filtered. The decanted organic phase from the filtrate was washed with sodium bicarbonate solution, dried, filtered and evaporated to dryness. The residue was chromatographed over silica gel and was eluted with a 9-1 benzene-ethyl acetate mixture. The product was crystallized from isopropyl ether to obtain 300 mg of 3-methoxy-20-formylimino-17α,21-diacetoxy-19-nor-$\Delta^{1,3,5(10)}$-pregnatriene. A sample was crystallized from a mixture of dichloromethane and isopropyl ether and then from methanol to obtain the product melting at 135° C.

Analysis: $C_{26}H_{33}O_6N$. Calculated: %C 68.55; %H 7.30; %N 3.07. Found: %C 68.4; %H 7.3; %N 3.0.

Step D:

3-methoxy-17α,21-diacetoxy-19-nor-$\Delta^{1,3,5(10)}$-pregnatriene-20-one

A solution of 120 mg of the product of Step C, 1 ml of water and 2 ml of acetic acid was heated to 100° C. for 3 hours in a bath and was then cooled and diluted with water. The mixture was extracted with dichloromethane and the organic phase was washed with water, dried and evaporated to dryness. The 100 mg of residue were chromatographed over silica gel and eluted with a 7-3 cyclohexane-ethyl acetate mixture. The 90 mg of product was crystallized from methanol to obtain 55 mg of 3-methoxy-17α,21-diacetoxy-19-nor-Δ$^{1,3,5(10)}$-pregnatriene-20-one melting at 162° C.

Step E:

3-methoxy-19-nor-Δ$^{1,3,5(10)}$-pregnatriene-17α,21-diol-20-one

Nitrogen was bubbled through a suspension of 980 mg of the product of Step D in 7 ml methanol for 15 minutes and the resulting suspension was cooled in an ice bath. 1 ml of potassium methanolate (15 g per 100 ml) was added thereto and the mixture was stirred under nitrogen in an ice bath for one hour. 0.2 ml of acetic acid were added to the mixture which was diluted with water and extracted with dichloromethane. The organic phase was washed with water, dried and evaporated to dryness under reduced pressure. The 840 mg of residue were chromatographed over silica gel and eluted with a 7-3 benzene-ethyl acetate mixture to obtain 535 mg of 3-methoxy-19-nor-Δ$^{1,3,5(10)}$-pregnatrien-17α,21-diol-20-one. After crystallization from aqueous ethanol and then dichloromethane, the product melting at 177° C.

Analysis: $C_{21}H_{28}O_4$. Calculated: %C 73.22; %H 8.19. Found: %C 73.1; %H 8.4.

Various modifications of the process and products of the invention may be made without departing from the spirit or scope thereof and it is to be understood that the invention is intended to be limited only as defined in the appended claims.

What we claim is:

1. A process for the preparation of 17β-hydroxyacetyl-17α-ol steroids of the formula

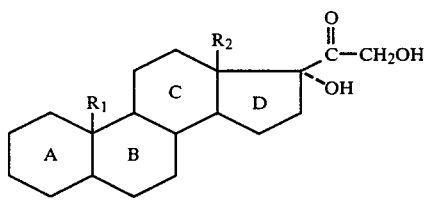

wherein $R^1$ is selected from the group consisting of hydrogen, alkyl of 1 to 4 carbon atoms optionally substituted with halogen or an oxygen or nitrogen function and alkenyl and alkynyl of 2 to 4 carbon atoms, $R_2$ is alkyl of 1 to 4 carbon atoms and the A,B,C, and D rings may contain one of more double bonds and are optionally substituted with at least one member of the group consisting of hydroxy, keto, halogen, alkyl and alkoxy of 1 to 4 carbon atoms and alkenyl and alkynyl of 2 to 4 carbon atoms comprising reacting a compound of the formula

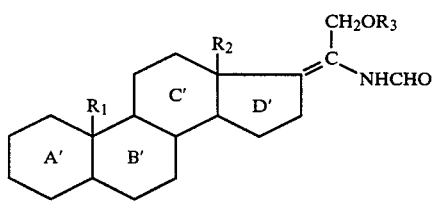

wherein $R_1$ and $R_2$ have the above definition, $R_3$ is selected from the group consisting of hydrogen and $R_3'$, $R_3'$ is a group protecting the hydroxyl and A', B', C' and D' have the same definition as A, B, C and D with the supplemental possibility of being substituted with a protected hydroxyl or protected ketone with a reactant capable of introducing an acetoxyl group selected from the group consisting of lead tetraacetate and idosobenzene diacetate to obtain a compound of the formula

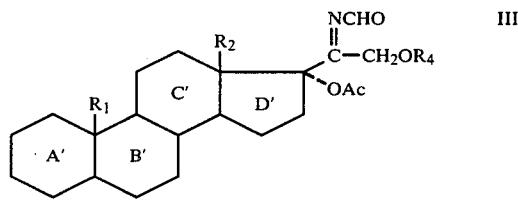

wherein $R_4$ is selected from the group consisting of $R_3'$ and acetyl and Ac is acetyl, reacting the latter with a hydrolysis agent to obtain a compound of the formula

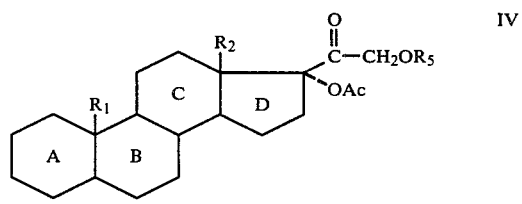

wherein $R_1$, $R_2$, A,B,C and D have the above definitions and $R_5$ is selected from the group consisting of hydrogen, a non-easily hydrolyzable hydroxy protective group and an acetyl group and reacting the latter to eliminate the acetyl group in the 17α-position and the $R_5$ group where it is other than hydrogen to obtain the corresponding compound of formula I.

2. The process of claim 1 wherein $R_2$ is methyl and $R_1$ is selected from the group consisting of hydrogen, methyl and ethynyl.

3. A process for the preparation of compounds of the formula

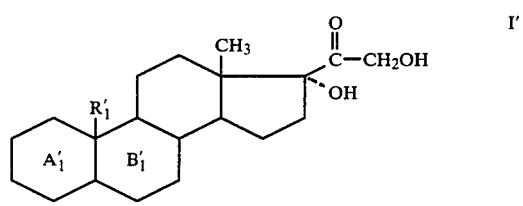

wherein $R_1'$, $A_1'$ and $B_1'$ form a ring system selected from the group consisting of

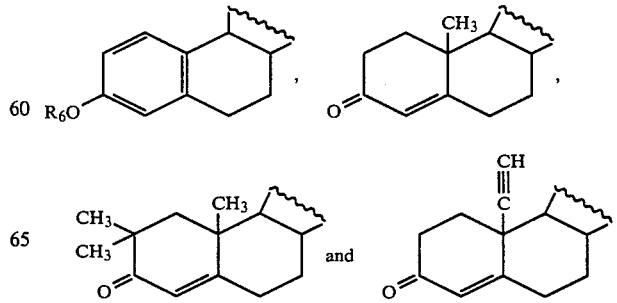

and R₆ is selected from the group consisting of alkyl of 1 to 8 carbon atoms and aralkyl of 7 to 12 carbon atoms comprises reacting a compound of the formula

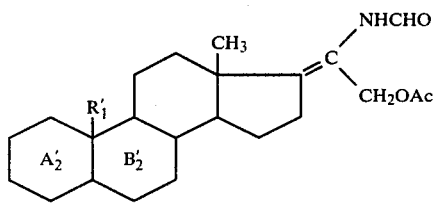

wherein the R₁', A₂' and B₂' form a group selected from the group consisting of

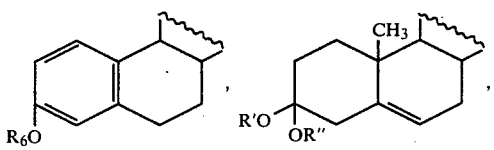

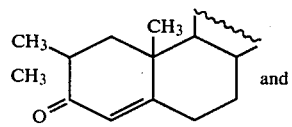

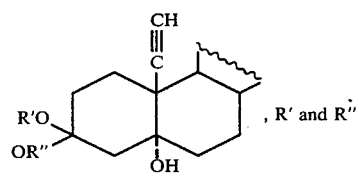

are individually selected from the group consisting of methyl and ethyl or taken together are ethylene or trimethylene and Ac is acetyl with a reactant capable of introducing an acetoxy group to obtain a compound of the formula

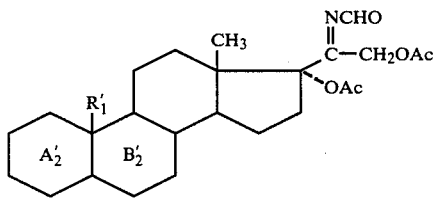

wherein R', Ac, A₂' and B₂' have the above definition and reacting the latter with a hydrolysis agent to obtain a compound of the formula

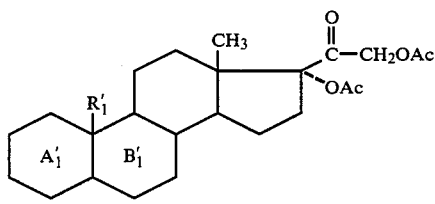

and saponifying the latter to obtain the corresponding compound of formula I'.

4. The process of claim 1 wherein the starting compound has the formula

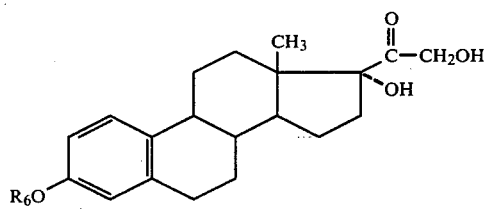

wherein R₆ is selected from the group consisting of alkyl of 1 to 8 carbon atoms and aralkyl of 7 to 12 carbon atoms.

5. The process of claim 1,2,3 or 4 wherein the reactant to introduce the acetoxy group is lead tetraacetate.

6. The process of claim 3 or 4 wherein R₆ is methyl.

7. The process of claim 3 wherein R' and R" form ethylene.

8. A compound having a formula selected from the group consisting of

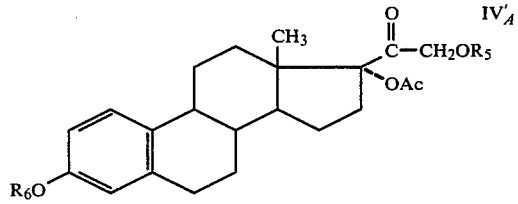

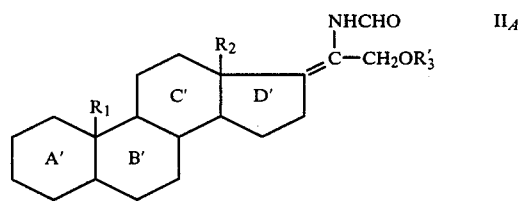

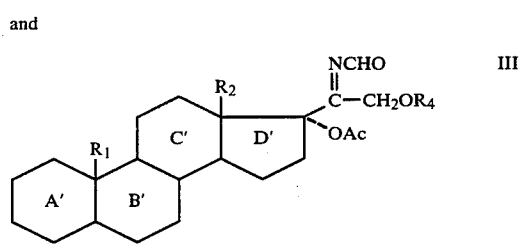

wherein R₁ is selected from the group consisting of hydrogen, alkyl of 1 to 4 carbon atoms optionally substituted with halogen or an oxygen or nitrogen function and alkenyl and alkynyl of 2 to 4 carbon atoms, R₂ is alkyl of 1 to 4 carbon atoms and the A', B', C' and D' rings may contain one of more double bonds and are optionally substituted with at least one member of the group consisting of hydroxy, keto, halogen, alkyl and alkoxy of 1 to 4 carbon atoms and alkenyl and alkynyl of 2 to 4 carbon atoms, R₃' is a group protecting the hydroxyl, R₄ is selected from the group consisting of R₃' and acetyl, Ac is acetyl and R₅ is selected from the group consisting of hydrogen, a non-easily hydrolyzable hydroxy protective group and an acetyl group.

9. A compound of claim 8 of formula II_A and III wherein R₃' and R₄ are both acetyl and the C' and D' rings are not substituted.

* * * * *